United States Patent [19]
Nowacki et al.

[11] Patent Number: 5,399,146
[45] Date of Patent: Mar. 21, 1995

[54] ISOCENTRIC LITHOTRIPTER

[76] Inventors: Christopher Nowacki, 1552 Chickamauga La., Long Grove, Ill. 60047; Mark T. Horbal, 2 S. 530 Iroquois Courts W., Warrenville, Ill. 60555

[21] Appl. No.: 166,072

[22] Filed: Dec. 13, 1993

[51] Int. Cl.⁶ .............................................. A61B 17/22
[52] U.S. Cl. ....................................... 601/4; 128/653.1
[58] Field of Search ...................... 128/653.1, 660.03; 601/2–4; 607/97; 378/195–197

[56] References Cited

U.S. PATENT DOCUMENTS

| | | | |
|---|---|---|---|
| 4,914,588 | 4/1990 | Schittenhelm | 601/4 |
| 4,984,575 | 1/1991 | Uchiyama et al. | 128/660.03 |
| 5,060,650 | 10/1991 | Wurster et al. | 601/4 |
| 5,240,002 | 8/1993 | Brisson et al. | 128/660.03 |

*Primary Examiner*—Ruth S. Smith
*Attorney, Agent, or Firm*—Robert M. Wolters

[57] ABSTRACT

An extracorporeal isocentric lithotripter is presented having a common isocentric axis of rotation. The patient having a bodily concretion to be destroyed lies on a table which is movable to position the concretion on the isocentric axis. An X-ray emitter and an image intensifier lie on a common diameter which is rotated about said isocentric axis to position said X-ray apparatus and said image intensifier in at least two positions to ascertain the location of the concretion. A shockwave lithotripter shockhead is mounted on a support rotatable about said isocentric axis to align said shockhead with said bodily concretion. The shockhead is mounted on said rotatable support by a double pivot arrangement to bring the second focus point of said reflector into coincidence with said bodily concretion for destruction of said concretion.

9 Claims, 3 Drawing Sheets

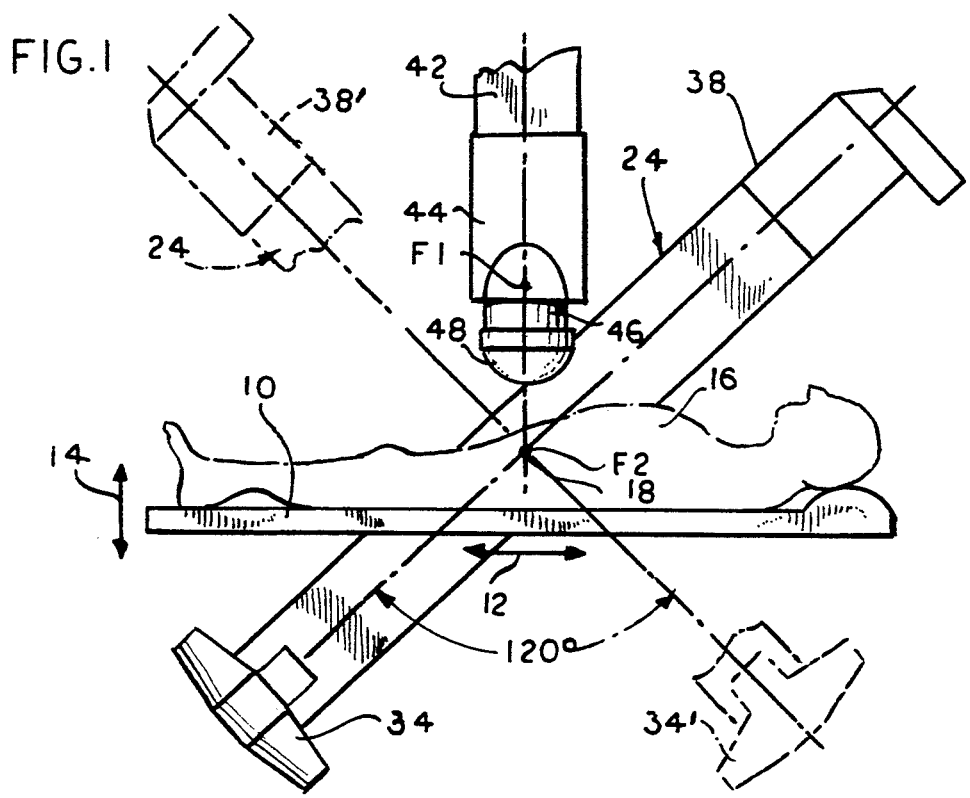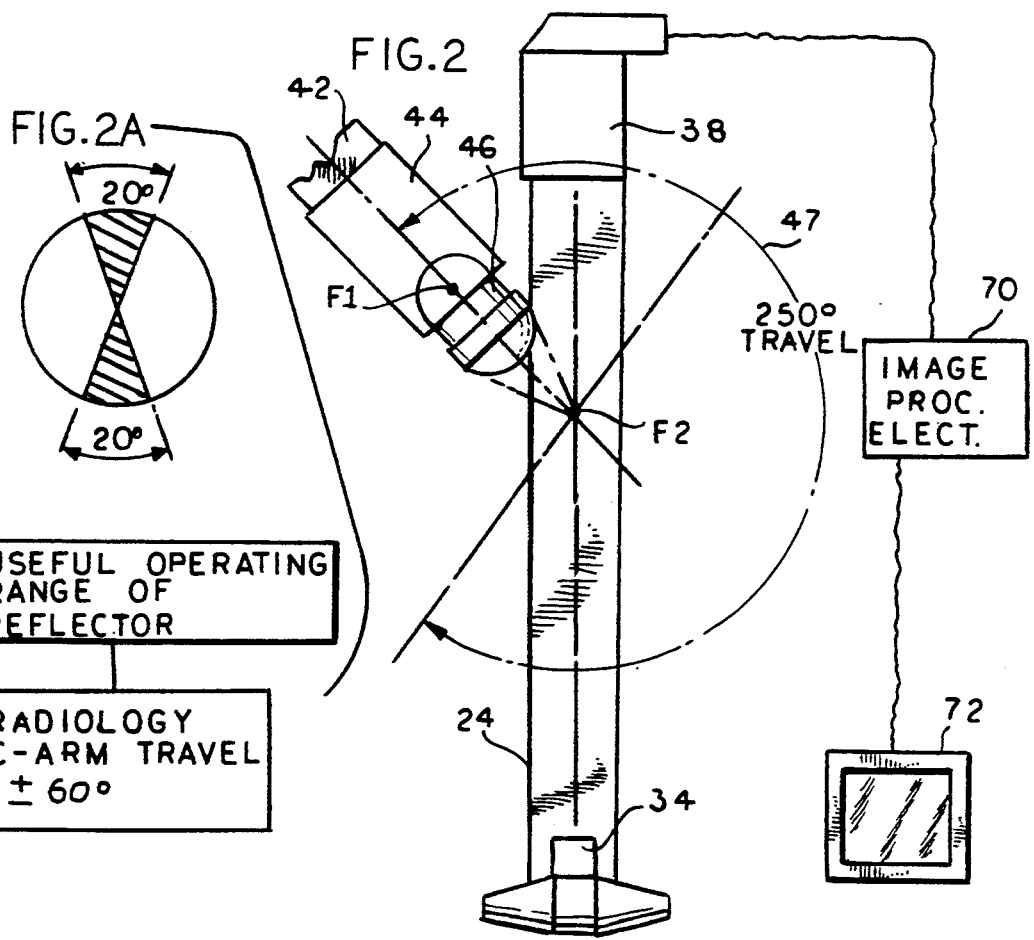

ISOCENTRIC LITHOTRIPTER

BACKGROUND OF THE INVENTION

The present invention relates to an extracorporeal lithotripter. Such lithotripters are known in the art, and utilized an ellipsoidal reflector. An ellipsoid will be recognized as a solid of revolution with two focal points. The ellipsoidal reflector is truncated short of the second focal point. A rubber or the like diaphragm closes the open end of the ellipsoidal reflector. The reflector is filled with water with a saline content, and a spark gap is provided at the first focus point in the reflector. The reflector is positioned adjacent a body having a kidney stone or other concretion to be disintegrated. The diaphragm presses against the body, and the second focal point of the ellipsoidal reflector is brought into coincidence with the kidney stone or other concretion. High voltage pulses produce sparks across the spark gap. These, in turn, flash some of the water into steam, and may also cause some dissociation of the hydrogen and oxygen. The result is a series of shockwaves or pulses. These shockwaves are focused by the walls of the reflector and pass through the water in the reflector, through the diaphragm, which is pressed against the skin of the body, and through the tissues of the body to focus on the second focus point coincident with the kidney stone or other concretion. A series of such shocks, generally less than an hour for a treatment, result in reduction of the stone to small particles which pass from the body with the urine.

Such treatment is effected from exteriorly of the body, and it may require no hospitalization, or sometimes merely overnight hospitalization. Advantages of a lithotripter with an isocentric system have previously been recognized, for example see Puppo U.S. Pat. No. 5,230,329. In such an isocentric system the reflector, often referred to as the shockhead, and the aiming or localization device or devices, such as an X-ray system are supported for rotation about a common center. The concretion to be destroyed is positioned on this center, and the aiming system can be moved to locate the stone from different angles, and the shockhead can be moved to cause the shockwaves to attack the concretion from different angles, thereby hastening destruction thereof. In the system disclosed by Puppo in U.S. Pat. No. 5,230,329 the aiming or localization system, and the shockhead are mounted on a common ring. This has advantages in rigidity and balance. However, other advantages can be realized by separately mounting the shockhead and the localization system for independent rotation about a common center. Independent movement of the radiological localization or aiming apparatus and of the shockhead, both aimed at the isocenter of the system permits the doctor or clinician to choose the most convenient angle of approach to the patient by simple positioning of the shockhead. For example, the patient can be treated in supine, prone, or lateral positions with a choice of dorsal, ventral or lateral approach. The patient is not moved between localization and treatment, thus insuring high accuracy of the stone localization process. Localization is effective by means of fluoroscopic or X-ray techniques. This is done by making a biplane sighting of the calculus at two different angles, and centering the target in each. Initially, the radiological axis is placed in a vertical position and the table supporting the patient is moved horizontally in order the center the stone in the field of view. At this point, the stone lies on the vertical axis of the system. Subsequently, the fluoroscopy apparatus is moved to an arbitrary position, and a second sighting is made. The table then is moved only vertically to center the stone, bringing it into focus. It be emphasized that this is also the treatment position. The patient is not moved thereafter. This method of localization is rapid, and does not suffer from any loss of accuracy caused by excessive patient movement. The angle between the two radiological projections is not fixed, but can be suitably chosen by the physician to reflect clinical needs.

OBJECTS AND SHORT SUMMARY OF THE PRESENT INVENTION

It is an object of the present invention to provide an extracorporeal lithotripter having an isocentric system with independent rotation of the shockhead and the X-ray aiming system.

An ancillary object of the invention is to provide means for axially shifting the shockhead so that the radiological aiming system and the shockhead can be rotated independently without interference with one another.

In effecting the foregoing objects, we provide two supporting arms rotatable about a common center. The radiological apparatus includes an X-ray tube and a fluoroscopic target mounted diametrically opposite to one another on the opposite ends of one of the arms and on a common diameter through the isocenter. The shockhead is mounted on another arm, so that it is axially movable to provide clearance between the aiming system and the shockhead.

Specifically, the shockhead is mounted by means of a pivot moveably mounted relative to a rotatable arm with the pivot being axially moveably toward and away from the isocenter in a common plane perpendicular to the isocenter. The shockhead further is mounted by a pivoted arm connected to the shockhead and to the moveable arm. Movement of the first mentioned pivot toward and away from the isocenter causes the shockhead to move in a pivoted or arcuate manner axially of the isocenter so that the shockhead can be retracted from the plane of the radiological system, or placed within such plane to permit movement of the radiological system and the shockhead independently of one another, or to move the shockhead into operating position substantially within such plane.

DESCRIPTION OF THE DRAWINGS

FIG. 1 is a diagrammatic side view showing the concept of the moveable patient table, and movement of the locating device and positioning of the shockhead for concretion destruction;

FIG. 2 is a view similar to FIG. 1, but absent the patient and table to illustrate further aspects of the invention;

FIG. 2a is a front view illustrating the useful operating range of the shockhead including the reflector;

DETAILED DESCRIPTION OF THE ILLUSTRATED EMBODIMENTS

Figure 3:
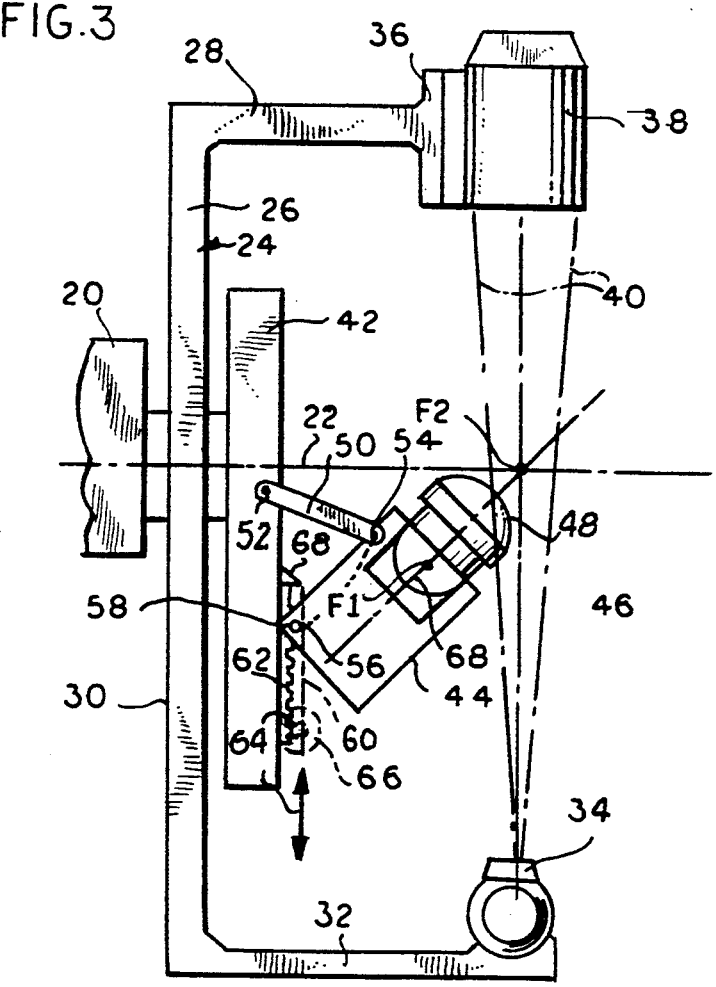
FIG. 3 is another somewhat diagrammatic representation corresponding to FIGS. 1 and 2, but taken at right angles thereto.

Attention first should be directed to FIGS. 1-3 for an understanding of the concept of the present invention. Structural details are better shown in FIGS. 4-6, and will be referred to later. A patient supporting table 10 is shown in FIG. 1. The table is radiotransparent so that X-rays can readily pass through it. The table is adjustable lengthwise as indicated by the arrows 12, and is also adjustable vertically as indicated by the double arrow 14. Such movement is effected by toothed rack and motor driven pinon arrangements which are known. A patient indicated at 16 lies on the table for destruction of a kidney stone or the like 18.

The patient and table are omitted from FIGS. 2 and 3 for clarity of illustration. The structure, as shown somewhat schematically in FIGS. 1-3, includes a main support 20 having a center line or axis of rotation 22. A substantially U-shaped support 24 is rotatably supported by a suitable shaft on the axis of rotation 22, which shaft is rotatable from within the support 20 by means of conventional electric motor and gear drive. The U-shaped arm or support 24 includes an upwardly extending portion 26 having a branch arm 28 extending parallel to the axis of rotation 22 in a direction away from the main support 20. The arm 24 further has a downwardly directed arm 30 formed integrally with the arm 26 and in a straight line therewith. It will be understood that the reference to up and down is with regard to the apparatus as illustrated in FIG. 3. A lower horizontal arm 32 extends from the lower end of the arm 30. The arm 32 at the end thereof suitably supports an X-ray tube or radiation emitting device 34 that is aimed inwardly of the U-shaped arm or support 24 to intersect the axis of rotation or center line 22. A support 36 is provided at the end of the arm 28 and suitably supports an image intensifier 38 which is located directly opposite the X-ray tube 34, and receives X-ray radiation as indicated generally by the lines 40 after it has passed through the body of the patient 16. In FIG. 1 it will be seen that the operating range of the X-ray tube and of the image intensifier is about 120°, i.e. 60° to either side from the vertical. The X-ray tube or apparatus is illustrated in one position at an extreme at 34, and at the other extreme at 34'. Similarly, the image intensifier is moveable from one extreme at 38 to the other extreme at 38'. Locating the stone 18 from two different positions determines precisely where the stone is in the patient's body.

With specific reference to FIG. 3, there is seen a second rotary support 42 which also is rotatable about the center line or axis of rotation 22. As will be understood, this is readily accomplished by having a hollow shaft supporting the U-shaped rotatable support 24 with a second shaft extending through it to the rotatable support 42. Different gearing is provided for rotating the two shafts, by way of electric motors as prime movers. The rotatable support 42 carries a shockhead 44 having a truncated ellipsoidal reflector 46. The rotatable support member 42 as is indicated in FIG. 2 is rotatable over an arc of about 250°, indicated by the arcuate line 47. This allows the shockhead to be used either from above the patient, or below the patient. For kidney stone destruction the useful operating range of the shockhead and reflector is about 20°, as indicated in FIG. 2a.

The reflector 46 is generally of known construction, having a first focal point indicated at F-1 and a second focal point F-2 disposed beyond the end of the reflector, and intended to be rendered coincident with the kidney stone 18. As is conventional, the open truncated end of the reflector is closed by a rubber or the like diaphragm 48 intended to engage the body of the patient. As is known, the reflector includes a pair of electrodes defining a spark gap located at the first focal point F-1. A series of high voltage electrical discharges across the spark gap results in a succession of shockwaves which are focused by the walls of the ellipsoidal reflector on the second focus point F-2, the shockwave passing through the water in the reflector and diaphragm, and through the diaphragm to the patient's body and focused on the kidney stone.

As is seen in FIG. 3 the shockhead is mounted by means of a link 50 pivotably secured to the rotatable support 42 at one end, and pivotably connected to the shockhead 54 relatively toward the upper end thereof, with the parts positioned as seen in FIG. 3. The shockhead further is connected by a pivot at the lower corner 56 to a pivot support 58 on a rack 60 suitably mounted for linear movement up and down the support 42. The rack 60 is provided with teeth 62 which mesh with a spur gear 64 driven by a reversible electric motor 66. An upstop 68 is provided for the rack 60.

With the rack and shockhead in limited upward position as shown in FIG. 3, the diaphragm 48 impinges against the body of the patient, and the second focus point F-2 is coincident with the kidney stone due to location of the kidney stone on the center line 22 by movement of the table 10.

The pivotable mounting of the shockhead is important, since, as just noted, in raised position it positions the second focus point F-2 on the kidney stone. With the rack in lowered position the shockhead lies flat against the rotatable support 42. The shockhead is then positioned away from the patient so that shockhead may move as desired without possible engagement (while moving) with the patient. Furthermore, it is completely out of the way of the support arm 24. The support arm 24 has been referred to as U-shaped, but with the parts positioned as in FIG. 3, it is better referred to as a C-shaped support.

Independent rotation of the X-ray tube and image intensifier relative to the shockhead is readily effected. The C-arm 24 is supported from within the support by a hollow shaft driven by a reversible electric motor and suitable gearing. A solid shaft extends from within the support through the hollow shaft to the rotatable support 42, and is driven by independent gearing and a reversible electric motor.

Figure 4:
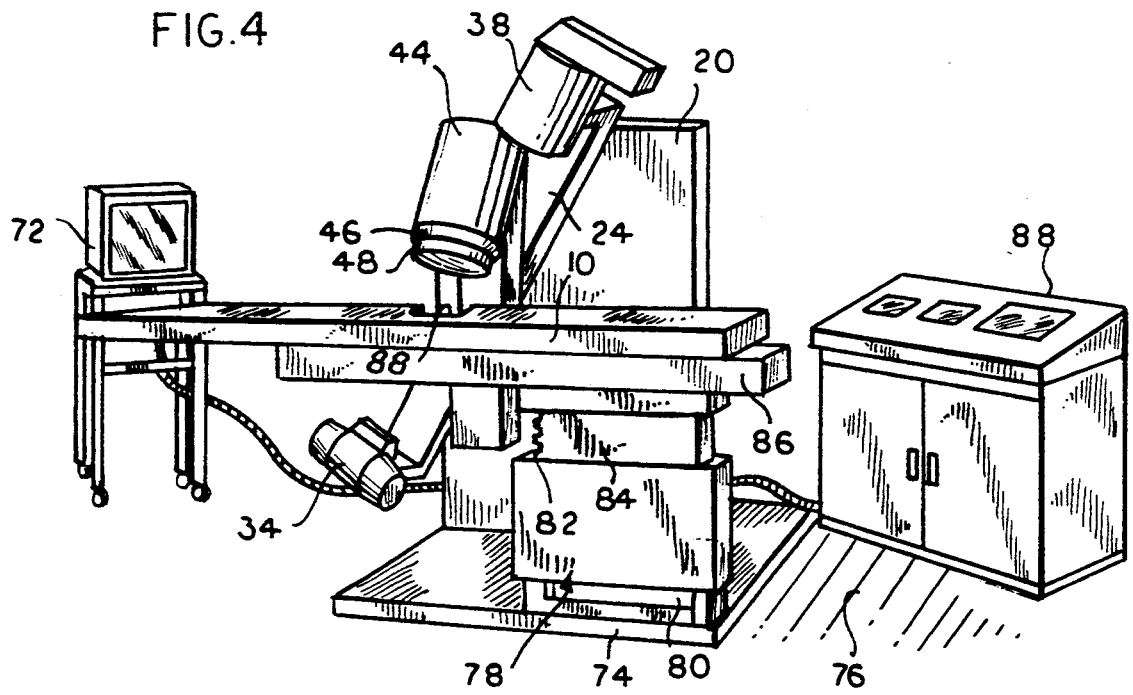
FIG. 4 is a perspective view of an actual machine constructed in accordance with the principles of the invention and showing also a computer control table and a monitor.
Figure 5:
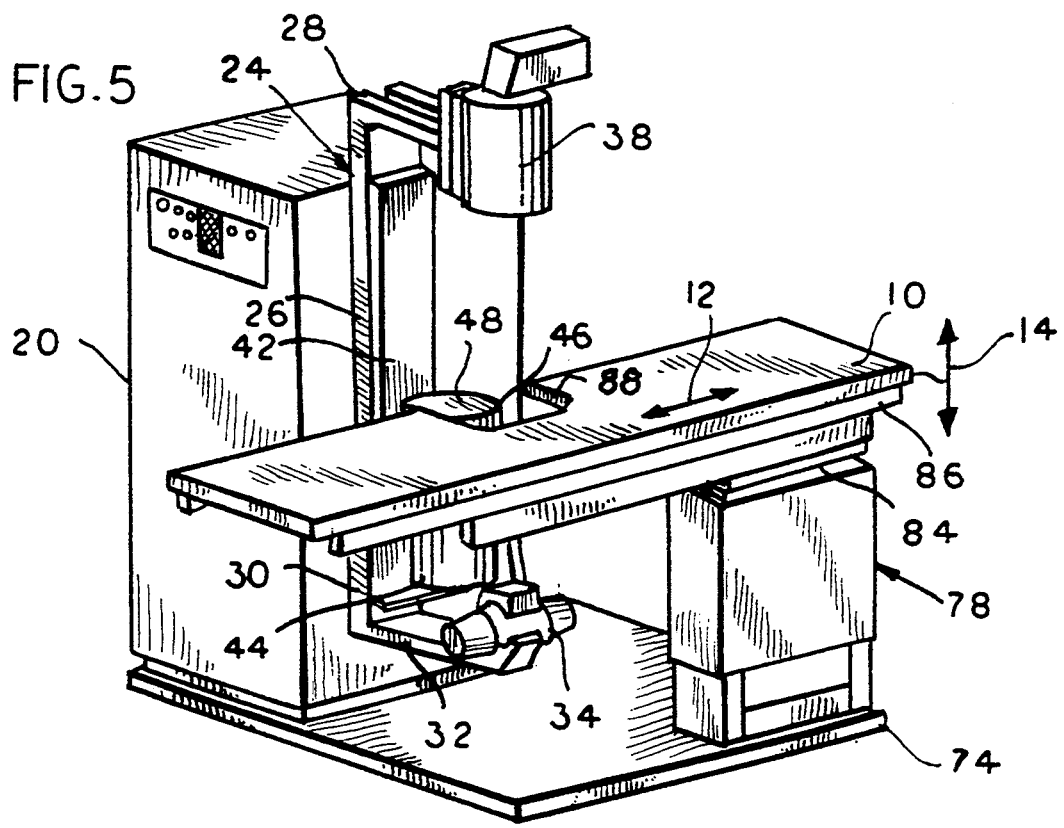
FIG. 5 is another perspective view taken from a different perspective, and with the aiming system and shockhead in a different position.
Figure 6:
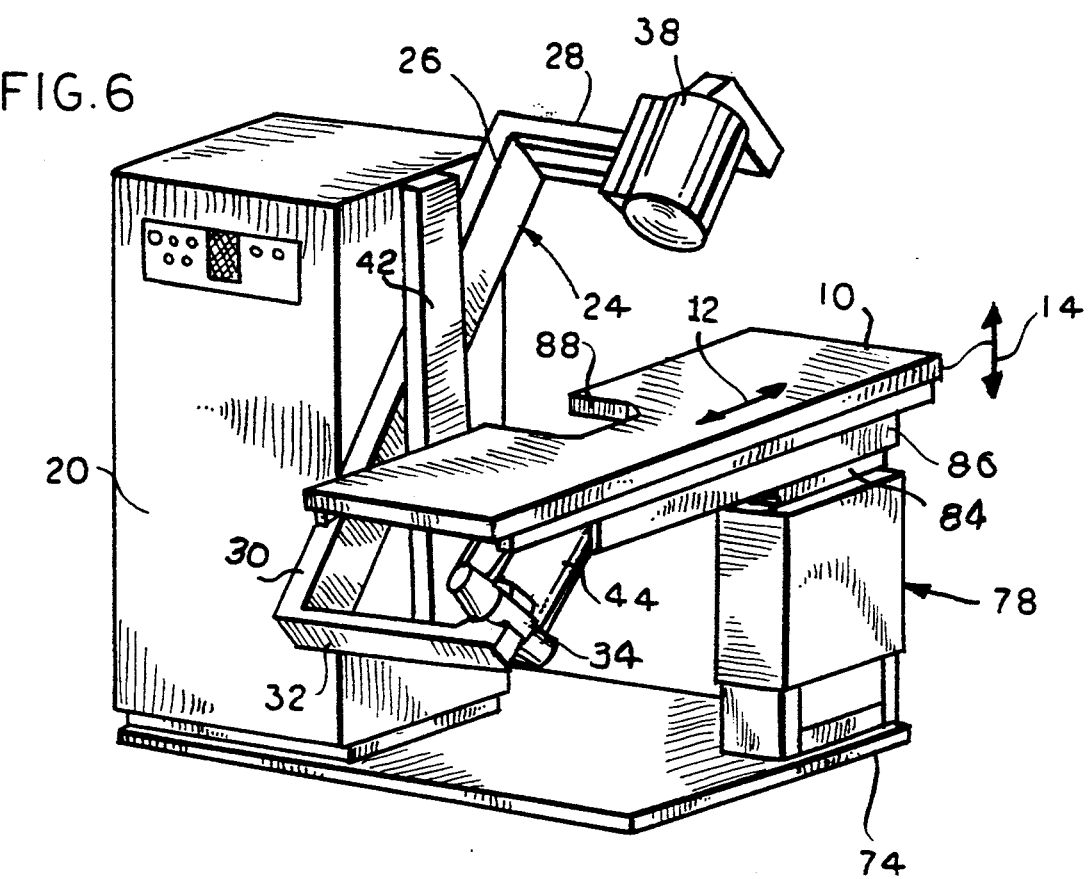
FIG. 6 is a view similar to FIG. 5, but showing the aiming system in a different position, and the shockhead moved into operating position.

The isocentric lithotripter of the present invention has now been conceptually disclosed. Certain details of construction are shown in FIGS. 4-6. The same numerals are utilized as heretofore, and complete redescription therefore is unnecessary. However, certain further details will be described. The lithotripter is readily placed in an existing room without necessity of revising the architecture or construction of the existing room. To this end, the lithotripter is provided with a flat base or platform 74 which is simply placed on the existing room floor 76. The support 20 heretofore disclosed is mounted on this platform. Also mounted on the platform is a telescoping, two part table support 78 which includes an outer fixed portion 80 containing a reversible electric motor and suitable gearing, including an output spur gear (not shown) engagable with the teeth 82 of a rack formed along the vertical edge of the inner telescoping portion 84 of the support.

The telescoping portion 84 at its upper end supports a horizontal table support structure 86 on which the patient supporting table 10 is moveable lengthwise by suitable structure such as a rack on the underside of the table engaging the teeth of a spur gear driven by a reversible electric motor.

The table 10 as previously has been disclosed is constructed of radiotransparent material to allow X-ray viewing of the kidney stone or other concretion. The table is of generally elongated shape, and is provided with a substantial edge cut out 88 over which the patient lies to allow access of the diaphragm 48 of the reflector 46 to the patient's body when approached from below, rather than above.

Positioning of the kidney stone by lengthwise and vertical adjustment, positioning of the shockhead to clear the patient, or to effect engagement with the patient, and movement of the X-ray emitter and image intensifier could all be effected manually, but preferably are effected much more quickly by use of a computer 88 shown in FIG. 4.

Although the C-arm 24 is rotatable, the X-rays emitted by the X-ray tube at all times pass through the center line or axis of rotation of the C-arm, whereby two X-ray views of the kidney stone permit manipulation of the table to place the kidney stone precisely on the center line. The patient may move himself laterally to insure that the stone will be on the center plane of the X-ray apparatus to insure positioning of the stone properly. The construction of the support 42 and the moveable, pivotable support of the shockhead insures that the second focus point F-2 the reflector will always lie on the center line or axis of rotation 22 to insure that the second focus point F-2 will always lie in coincidence with the kidney stone when the kidney stone has been positioned on the center line.

Due to the isocentric nature of the lithotripter this is true whether the shockhead is above the patient as in FIGS. 1 and 4 or below the patient, as in FIGS. 5 and 6.

Although reference has been made to X-ray or fluoroscopic location and viewing of the kidney stone, it is sometime preferable to use ultrasound, and this would be positioned similarly to the disclosed X-ray apparatus,.for revolving or turning about the isocenter of the apparatus.

Pendulum movement, either below or above the patient, of the shockhead over an arc of a few degrees leaves the reflector at all times focused on the kidney stone, due to the isocentric geometry of the lithotripter. Such movement allows slightly different engagement of the shockwaves with the kidney stone, and this has been found to produce more rapid fragmentation of the stone than a fixed approach.

The specific example of the invention as herein shown and described is for illustrative purposes only. Various changes may occur to those skilled in the art, and will be understood as forming a part of the present invention insofar as they fall within the spirit and scope of the appended claims.

The invention is claimed as follows:

1. An extracorporeal isocentric lithotripter comprising a table for supporting a patient having a bodily concretion to be destroyed, means for emitting radiation to determine the location of the concretion to be destroyed in a patient on said table, a base support, means on said base support for supporting said radiation emitting means for rotation about an isocentric axis, means for moving the patient on said table to position said concretion on said isocentric axis, a reflector having a first focus point within said reflector and a second focus point exteriorly of said reflector, means for mounting said reflector on said base support for rotation about said isocentric axis to a position on either side of said radiation emitting means, said reflector including means for generating shockwaves to destroy the bodily concretion, said reflector mounting means including means for moving said reflector rotationally about said axis and into engagement with the patient on said table and positioning said second focus point on said isocentric axis in coincidence with said concretion with shockwaves.

2. A lithotripter as set forth in claim 1 wherein the means for moving said reflector includes means for moving said reflector axially relative to said isocentric axis.

3. A lithotripter as set forth in claim 2 wherein said means for moving said reflector includes means for moving said reflector radially of said isocentric axis to move said second focus point between said isocentric axis and a position remote from said axis.

4. A lithotripter as set forth in claim 3 wherein said means for moving said reflector further includes means for pivotably moving said reflector.

5. A lithotripter as set forth in claim 1 wherein said means for moving said reflector includes means for moving said reflector radially of said isocentric axis to move said second focus point between said isocentric axis and a position remote from said axis.

6. A lithotripter as set forth in claim 1 wherein said means for moving said reflector includes a support rotatable about said isocentric axis, a link having two ends, one of said ends being pivotably connected adjacent one end of said support, and a pivot connection adjacent the other end of said support link pivotably connected to said reflector.

7. A lithotripter as set forth in claim 6 and further including a shockhead supporting said reflector, the pivot connection adjacent the other end of said link being pivotably connected to said shockhead at a predetermined position, and means linearly movable on said rotatable support and pivotably connected to said shockhead at a second position spaced from said predetermined position.

8. A lithotripter as set forth in claim 1 wherein said table is elongated in a predetermined direction to accommodate the patient, and further including means for moving said table in said elongated direction, and means for moving said table vertically to position said concretion on said isocentric axis.

9. A lithotripter as set forth in claim 8 wherein the means for moving the table in said elongated direction moves said table axially of said isocentric axis.

* * * * *